(12) United States Patent  
Ziegler

(10) Patent No.: US 7,820,104 B2  
(45) Date of Patent: Oct. 26, 2010

(54) TEST STRIP ANALYSIS APPARATUS

(75) Inventor: Walter Michael Ziegler, Munich (DE)

(73) Assignee: Iris Deutschland GmbH, Marburg (DE)

( * ) Notice: Subject to any disclaimer, the term of this patent is extended or adjusted under 35 U.S.C. 154(b) by 1070 days.

(21) Appl. No.: 10/496,205

(22) PCT Filed: Nov. 18, 2002

(86) PCT No.: PCT/US02/37179

§ 371 (c)(1),
(2), (4) Date: Mar. 23, 2005

(87) PCT Pub. No.: WO03/044500

PCT Pub. Date: May 30, 2003

(65) Prior Publication Data

US 2005/0163661 A1 Jul. 28, 2005

(30) Foreign Application Priority Data

Nov. 20, 2001 (DE) .................. 101 56 811

(51) Int. Cl.
*G01N 35/04* (2006.01)

(52) U.S. Cl. ............... 422/65; 422/63; 422/66; 422/68.1; 422/82.05; 436/44; 436/47; 436/164; 436/169; 356/213; 198/382

(58) Field of Classification Search ........... None
See application file for complete search history.

(56) References Cited

U.S. PATENT DOCUMENTS

| | | | |
|---|---|---|---|
| 2,828,917 A | 4/1958 | Wheeler et al. | |
| 3,890,509 A * | 6/1975 | Maxey | 250/559.25 |
| 4,689,202 A * | 8/1987 | Khoja et al. | 422/65 |
| 5,097,938 A * | 3/1992 | Gruner et al. | 198/397.04 |
| 5,244,077 A | 9/1993 | Deschner | |
| 5,341,915 A * | 8/1994 | Cordia et al. | 198/460.1 |
| 5,408,535 A * | 4/1995 | Howard et al. | 382/128 |
| 5,846,490 A * | 12/1998 | Yokota et al. | 422/66 |
| 6,199,679 B1 | 3/2001 | Heuft | |

FOREIGN PATENT DOCUMENTS

| | | |
|---|---|---|
| AU | 477 428 | 6/1975 |
| DE | 198 57 426 | 6/2000 |
| EP | 0 643 296 | 3/1995 |
| EP | 0 994 343 | 4/2000 |
| GB | 1 425 605 | 2/1976 |

* cited by examiner

*Primary Examiner*—P. Kathryn Wright
(74) *Attorney, Agent, or Firm*—DLA Piper LLP (US)

(57) ABSTRACT

A test strip analysis apparatus comprising a housing, an insertion station for receiving a test strip to be inspected, an optical measuring unit for measuring the test strip, a transport device for transporting the test strip from said insertion station to the optical measuring unit within the reaction period required for the test strip, and an analyzing unit for evaluating the measurement of the strip, wherein the transport device comprises first and second transport sections which are interconnected through a connecting region and can be driven independently of one another, with the first transport section being capable of transporting the test strip at a higher first transport speed from the insertion station to the connecting region, and the second transport section being capable of transporting the test strip at a slower second transport speed from the connecting region to the optical measuring unit.

14 Claims, 3 Drawing Sheets

TEST STRIP ANALYSIS APPARATUS

CROSS-REFERENCE TO RELATED APPLICATIONS

This application is the national phase of PCT application PCT/US2002/037179 having an international filing date of Nov. 18, 2002, which claims priority from German application number 101 56 811.8 filed Nov. 20, 2001. The contents of these documents are incorporated herein by reference.

FIELD OF THE INVENTION

The present invention relates to a test strip analysis apparatus for analyzing elongated test strips with at least one test field that is wetted with a liquid for detecting substances therein, whereupon the reflectivity or transmissivity of at least one test field changes during a specific reaction time in dependence on the concentration of the substance to be detected, said apparatus comprising:
a housing,
an insertion station for inserting a test strip wetted with the liquid to be inspected,
an optical measuring unit for measuring the test strip, and
a transport device for transporting the test strip from the insertion station to the optical measuring unit within the reaction period required for the test strip.

BACKGROUND OF THE INVENTION

Test strip analysis apparatus of this kind are used, for example, in a doctor's practice, in hospitals or medical laboratories where blood or urine are routinely inspected using test strips, and where therefore a large number of test strips must be analyzed. An advantage of a test strip analysis apparatus of the above-mentioned type is that a test strip may be inserted directly after wetting with the liquid to be inspected without requiring the lab technician to wait for the reaction period of the respective test strip to elapse. When a large number of strips must be analyzed this would indeed be a nuisance. In an analysis apparatus of this type, the reaction period is bridged by transport of the wetted test strip from the insertion station to the optical measuring unit.

In an analysis apparatus of the above-mentioned type the transport device usually is a conveyor or the like which extends between insertion station and optical measuring unit and on which the test strips, arranged thereon in a direction transverse to the transport direction, are transported. Between the insertion of two test strips at the insertion station one must wait at least till the measuring period is over that is required for measuring the test strip with the measuring unit. Since the measuring period is typically only a fraction of the test strip's reaction period a large number of test strips are present on the conveyor at the same time, namely as many test strips as measuring periods fit into the reaction period when the capacity of the analysis apparatus is optimally used.

Since a test strip analysis apparatus of this type should, however, be as compact as possible, the length of the conveyor is limited. Consequently, the test strips are very close to one another when the apparatus capacity is fully used and the measuring period is short. Thus, even when the measuring period is indefinitely short the maximum frequency at which the test strips may be placed onto the conveyor cannot be increased at will because, given the limited length of the conveyor, the strips successively placed onto the conveyor would be too close to one another. There would be the risk of two adjacent test strips contacting one another or lying crosswise because it is not always possible to manually place the test strips onto the conveyor such that they are exactly parallel to one another. Accordingly, in order to prevent successively loaded test strips from contacting one another they must be placed onto the conveyor with a certain minimum spacing. In view of the limited length of the conveyor and the fixed transport time (namely the reaction period), this constitutes a further limitation of insertion frequency.

In practical use, however, even the insertion frequency which is theoretically possible cannot be achieved with conventional test strip analysis apparatus. This is due to the fact that, even if a lab technician were capable of preparing the test strips on average at that speed at which they can at best be inserted into the analysis apparatus, the time for preparing the test strips is of course subject to variations. In case the lab technician has prepared two strips in extremely short time one after the other, he cannot insert them as closely behind one another as he wishes because the strips would come too close on the conveyor and would reach the measuring unit following one another too rapidly. Thus, the time gained during preparation of a first strip cannot compensate the time lost during slower preparation of a following strip, because the lab technician is forced to spend the time saved during preparation of the first strip waiting for the apparatus to be ready to receive this strip. On the whole, in practical use the inflexibility regarding the time of test strip insertion leads to a decrease of performance of conventional test strip analysis apparatus.

Moreover, operation of an apparatus of this type is very uncomfortable because the lab technician must concentrate on inserting the test strip at the optimum time if he wants the make full use of the apparatus' capacity.

BRIEF SUMMARY OF THE INVENTION

Accordingly, the invention was based on the object to provide a test strip analysis apparatus of the above-mentioned type wherein a certain period of time is available for inserting a test strip, even when the capacity of the apparatus is optimally used.

This problem is solved in a test strip analysis apparatus of the above-mentioned kind by the transport device comprising first and second transport sections which are interconnected through a connecting region and can be driven independently of one another, with the first transport section being formed to be capable of transporting an inserted test strip at a higher first transport speed from the insertion station to the connecting region, and the second transport section being formed to be capable of transporting the test strip at a slower second transport speed from the connecting region to the optical measuring unit, wherein passage through the second transport section takes at least approximately as much time as the reaction period of the test strip.

Since the transport device of the analysis apparatus according to the invention consists of two sections that can be driven independently of one another, the time at which a test strip is inserted is decoupled from the time at which a test strip reaches the optical measuring unit.

With the first transport device, a test strip can be quickly conveyed from the insertion station to the connecting region within a first time interval T1 and can be transferred to the second transport section. For the same reasons as in case of the conventional analysis apparatus a specific time T2 must elapse between two successive test strip transfer operations in order to have time for measuring the first test strip and to maintain a minimum distance between the test strips present on the second transport section.

The transport speed may be chosen so high that T1 is significantly smaller than T2. After transfer of a strip the first transport section must be stopped for a time interval of the duration T2−T1 during which a further test strip can be inserted before this test strip, too, can be transported to the connecting region within the time T1. Thus, a time T2−T1 is obtained during which a test strip can be inserted, even when the analysis apparatus capacity is optimally used.

In a preferred embodiment the first and second transport sections have at least two parallel continuous belts each, forming a conveying surface for a test strip placed across the belts, the conveying surfaces of the first and second transport sections being arranged in the same plane and adjoining one another in the connecting region.

Accordingly, with a transport mechanism of this type, the test strips are placed across the belts transversely with respect to the transport direction at the insertion station. In this connection, it is important that all test strips are deposited at least approximately perpendicular to the belts. Only then will the strips lie parallel without contacting or, even worse, crossing one another. The great advantage of the described structure using transport belts is, however, that a test strip accidentally put down obliquely in the first transport section will automatically be aligned in a direction at least approximately perpendicular with respect to the transport direction in the connecting region. This is to be understood as follows:

In case the test strip is accidentally put down not exactly transversely to the transport direction, but such that the first end thereof is ahead of the second end thereof by a certain length in transport direction, the first end of the test strip reaches the connecting region earlier than the second end. Consequently, the first end is transferred to a belt of the second transport section while the second end still rests on the belt of the first transport section. Since the first end moves at the slower second transport speed whereas the second end continues moving at the higher first transport speed, the delay of the second end with respect to the first one is mostly compensated, i.e. the strip is rotated towards a transverse position until the second end of the test strip, too, is transferred to a belt of the second transport section. The greater the difference between the first and second transport speeds, the more complete is the alignment.

Due to the strip alignment effected in the connecting region test strips that are successively inserted are arranged approximately parallel in the second transport section even if they had been inserted obliquely by mistake in the first transport section. Therefore, a higher strip density can be dealt with in the second transport section than in a conventional apparatus without the strips contacting or, even worse, crossing one another. Such test strip analysis apparatus according to the invention can also be designed to be more compact than a conventional analysis apparatus having the same maximum insertion frequency.

A further advantage of the use of transport belts is that they offer a minimum support surface for the test strips which are freshly wetted and thus moist; therefore, only a little of the liquid to be checked adheres to the belts. This is an important fact because larger amounts of remaining liquid could contaminate a test strip inserted at a later time. Bands or the like could be used instead of the belts.

In the connecting region, the two pairs of belts are preferably guided such that their curved portions lie at least approximately on a common cylinder surface. Here, it is most advantageous when the belts of the second transport section lie axially between the belts of the first transport section on the common cylinder surface, because test strip alignment in the connecting region has proven to work particularly well with an arrangement of this type.

In a preferred embodiment the transport device comprises first, second and third drums which are arranged parallel to one another in one plane, the belts of the first transport section being stretched between the first drum and freely rotating rollers integrated in the second drum and being driven by the first drum at the first transport speed, and the belts of the second transport section being stretched between the second and third drums and being driven by the second drum or the third drum at the second transport speed. This way the structure of a test strip analysis apparatus according to the invention is simple and can be obtained with a reduced number of components.

Preferably, the second transport section includes a third belt which is likewise stretched between the second and third drums and arranged axially between the first two belts, but runs in an annular groove provided in the second drum that has a depth such that the belt does not contact a test strip present in the connecting region. The third belt prevents the test strip from sagging in the second transport section. In the connecting region itself it is kept away from the test strip such that it cannot interfere with alignment thereof.

In an advantageous embodiment the two transport sections are driven by two independent driving elements. By virtue of two independent driving elements the first and second transport speeds may be chosen independently of one another and may be adapted to the respective demands. In an alternative embodiment the two transport sections are driven by a common driving element, wherein the differing transport speeds are obtained by a gear and the independence in driving is obtained by a clutch.

In a further preferred embodiment a stop element is provided in the region of the measuring unit, said stop element being movable between a blocking position wherein a test strip located on the conveying surface of the second transport section aligns with the measuring position while resting at the stop element and a release position wherein the test strip is released. With the help of such a stop element, the test strip can be stopped for a short time and can be measured by the optical measuring unit as it lies on the belts. In case a test strip has turned between connecting region and optical measuring unit, e.g. due to vibrations, it is re-aligned at the stop element. Preferably, the stop element is constituted by two parallel pins which are mounted in spaced relation to one another on a holding device arranged transverse to the transport direction and which project into the conveying surface of the second transport section when the stop element is in its blocking position.

In an advantageous further development the stop elements have further blocking positions wherein the parallel pins project into the conveying surface of the second transport section in various locations. Thus, the test strip may be stopped and aligned at one of a plurality of possible locations. This constitutes an advantage when test strips of different sizes are to be inspected using the same analysis apparatus. Furthermore, it is possible to analyze a test strip not only as a whole but also in several steps by measuring, for example, longitudinal portions of the test strip one after the other. This way the optical measuring unit can possibly be of simpler structure.

In a further preferred embodiment, the insertion station is defined by a slit formed in the housing through which a wetted test strip can be placed onto the conveying surface of the first transport section. Because of the slit it is easier to place the test strip on the conveying surface with approximately perpendicular orientation with respect to the transport direction.

Further, a sensor, e.g. a light barrier, is preferably provided for detecting a test strip at the insertion station. The sensor can be used to control driving of the first transport section. If a test strip is detected at the insertion station the controller causes the strip to be transported to the connecting region as soon as at least a period of time T2–T1 has elapsed after the preceding transport with the first transport section.

As long as there is a test strip present in the first transport section insertion of a further test strip is not allowed. Therefore, an indicator is preferably provided for indicating whether a test strip is present in the first transport section.

A further preferred embodiment provides a display panel and/or a printer. Thus, the analysis results can be read and recorded. It is further of particular advantage when the test strip analysis apparatus has means for connecting data input devices, in particular a barcode reader and/or a keyboard. These input devices can for example be used for inputting personal data related to the patient for whom the test strip is to be analyzed, and for recording the analysis result in relation with this data. The test strip analysis apparatus further has a recess at its lower surface for accommodating a keyboard.

Further advantages and features of the test strip analysis apparatus according to the invention will become apparent from the following embodiment, which is explained with reference to the accompanying drawings, wherein

DETAILED DESCRIPTION OF THE INVENTION

Figure 1:
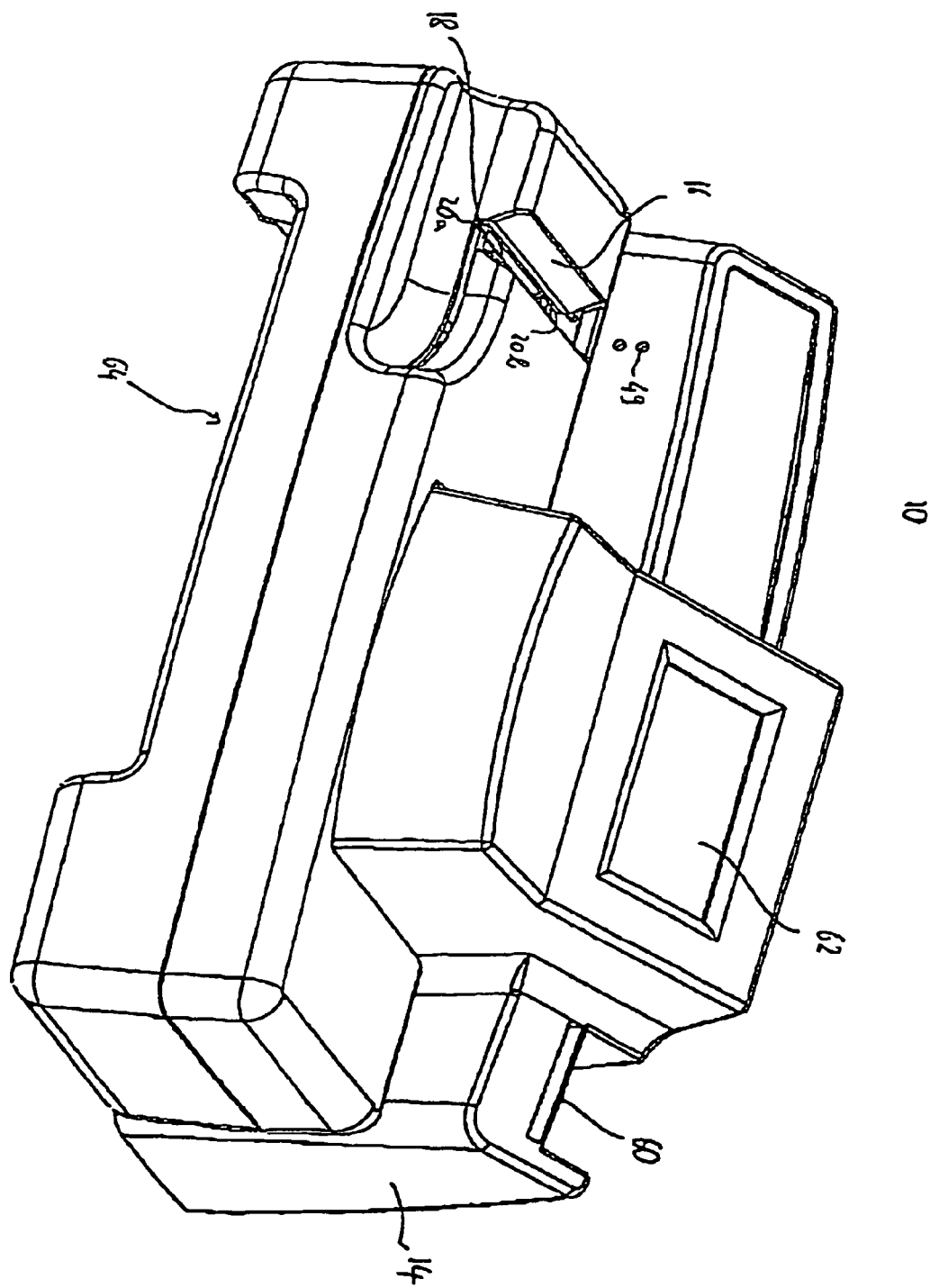
FIG. 1 is a perspective view of a test strip analysis apparatus according to the invention.
Figure 2:
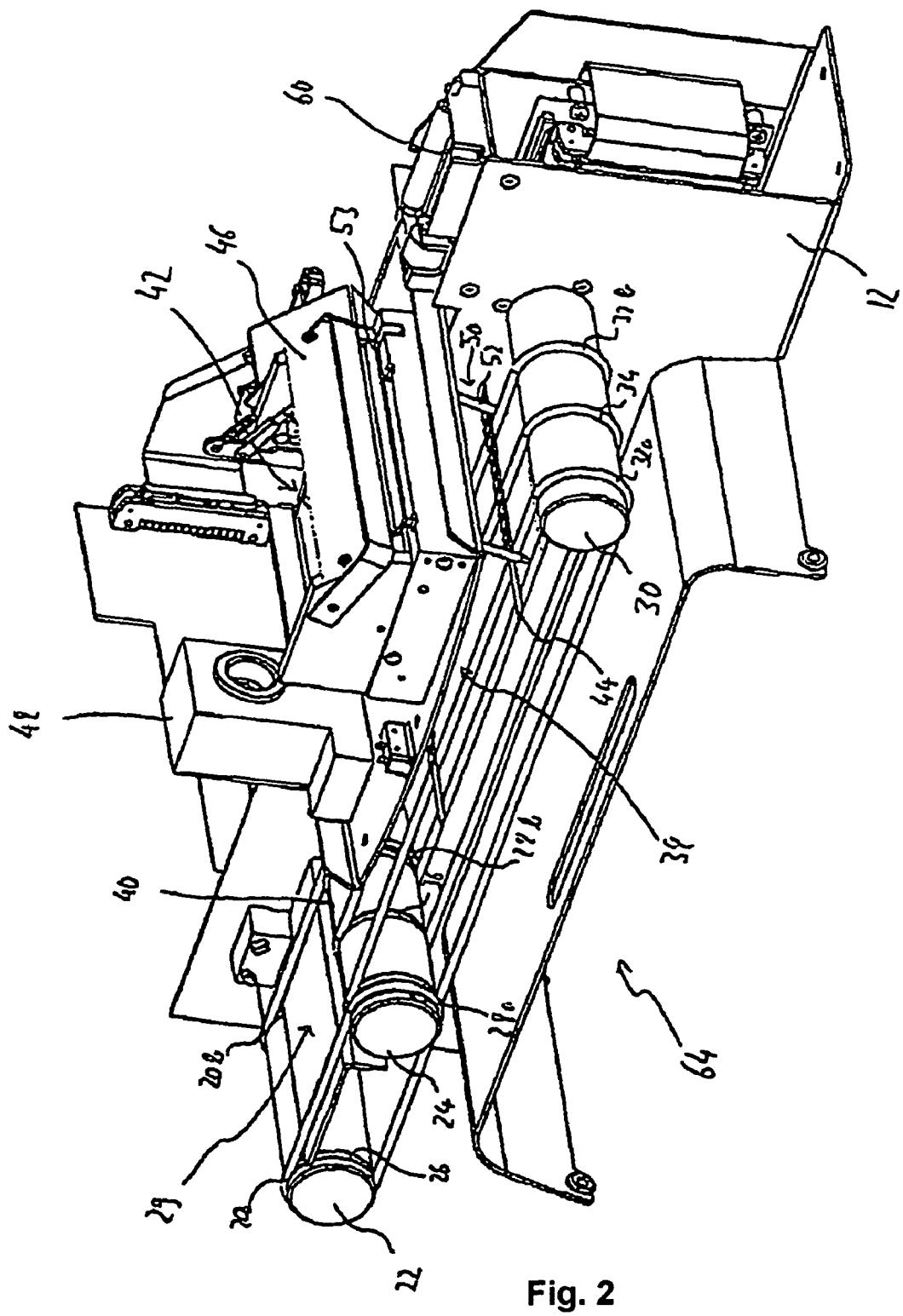
FIG. 2 is a perspective view of the analysis apparatus of FIG. 1 with the housing removed.

FIG. 1 shows a test strip analysis apparatus 10 according to the invention, comprising a housing 14 whereas FIG. 2 shows the same apparatus with the housing removed. A slit-like opening 16 is formed in the housing and defines an insertion station 18 for inserting a test strip. When a test strip to be analyzed is inserted the strip is placed in the slit 16 and is thereby positioned across two parallel continuous belts 20a, 20b, which are shown in FIG. 2. The pair of belts 20a, 20b is stretched between a first 22 and a second drum 24 mounted to a frame 12, wherein the belts rest on the first drum 22 in annular grooves 26. Freely rotating rollers 28a, 28b are integrated in the second drum 24; the belts 20a, 20b rest on said rollers. The first drum 22 is driven by a motor (not shown). The belts 20a, 20b, the drum 22 and the rollers 28a, 28b form a first transport section 29.

Further, a third drum 30 is mounted to the frame 12. A further pair of belts 32a, 32b is stretched between the second 24 and third drums 30 and rests on the two drums in annular grooves 26. A third belt 34 is located between the pair of belts 32a, 32b, and rests on the third drum 30 in an annular groove 26, too, but rests on the second drum 24 in an annular groove 36 which is deeper than the annular groove 26. The second drum 24 is driven by the same motor as drum 22, but independently thereof. The belts 32a, 32b and 34, the second 24 and third drums 30 form a second transport section 38. The apex line 40 of the second drum 24 defines the connecting region between the first and second transport sections.

An optical measuring unit 42 is located above the belts 32a, 32b and 34 in the vicinity of the third drum 30. This measuring unit 42 comprises an illumination device (not shown) suitable for illuminating a test strip arranged in the measuring position transversely across the belts 32a, 32b and 34. Via a mirror 46 the illuminated test strip 44 is imaged onto a planar sensor (not shown) provided in the sensor housing 48, and the test strip is evaluated in an evaluation unit (not shown) on the basis of the received image. In the measuring position, the test strip 44 rests at the pins 52 of a stop element 50 which are mounted in a spaced relation to one another on a holding device 53 orientated in a direction transverse to the transport direction.

In the illustrated test strip analysis apparatus 10 according to the invention, a test strip wetted with the liquid to be checked is transported from the insertion station 18 via the first 29 and second transport sections 38 to the measuring position in the region of the optical measuring unit 42 within the required reaction period. The function of the transport mechanism used is described below.

An indicator 49 is provided in the housing 14 and has two differently colored diodes which indicate whether a test strip is present in the first transport section, i.e. whether the analysis apparatus is ready to receive a test strip to be checked. When it is signaled that the apparatus is ready, a test strip can be placed transversely across the belts 20a, 20b through the slit 16 provided in the housing 14 at the insertion station 18. The apparatus is ready for test strip insertion as soon as the previously inserted test strip has left the first transport section. The first transport section can be driven by the drum 22 at a first transport speed, which is comparatively high. Thus, an inserted test strip can be quickly conveyed from the insertion station 18 to the connecting region 40 within the time interval T1.

The second transport section 38 is driven by the second drum 24 at a slower second transport speed. In the illustrated apparatus, transport from the connecting region 40 to the measuring position takes as much time as the reaction period of the test strip used, which is typically about one minute. Since, on the other hand, the apparatus on the whole is rather compact, the spatial length of the second transport section, and consequently the second transport speed, is very small.

Since measuring of the test strip by means of the measuring unit 42 takes only a fraction of the reaction period, a large number of test strips are present in the second transport section at the same time when the analysis apparatus is optimally utilized. The frequency at which successive test strips are transferred onto the second transport section is limited by the measuring period on the one hand, and on the other hand by the fact that due to the limited spatial length of the second transport section the number of test strips which may be present in the second transport section at the same time is limited, because otherwise the test strips would be too close to one another and would contact or, even worse, cross one another. In any case, the time between two test strip transfers from the first to the second transport section must not fall below the resulting interval T2.

When the analysis apparatus capacity is optimally used, the test strip transfer to the second transport section is thus effected with a rigid predetermined cycle having an interval length of T2. The first transport speed, however, is chosen so high that the transport time in the first transport section T1 is significantly smaller than T2. As a consequence, the user inserting successive test strips is not bound to the rigid cycle under which the analysis apparatus can process test strips when its capacity is optimally used. In case, for example, a first inserted test strip is transported to the connecting section immediately after insertion, the belts of the first transport section can be stopped already after the time T1 and a second test strip can be inserted. The second test strip remains at the insertion station for the duration of the time difference T2−T1 before the first transport section is again activated and the second test strip is transported to the connecting region. In case the operator has prepared the second test strip in an extremely short time he can insert the strip already after the time T1 following the first one and must not wait for the complete time T2 to elapse. Now, there is more time available for preparing a third test strip, namely 2*T2−T1. Thus, time gained during quick preparation of a test strip can compensate for time lost during slow preparation of a following test strip, whereby the performance of the test strip analysis apparatus is noticeably increased in practical use. Moreover, flexible insertion is much more comfortable for the operator than being bound to a rigid insertion cycle.

As mentioned above, the interval length T2 cannot be rendered indefinitely small because otherwise the test strips in the second transport section would be too close to each other and could contact or cross one another. In the illustrated test strip analysis apparatus according to the invention, however, the test strips in the second transport section can be closer to one another than in conventional apparatus without the risk of contact therein between. This is due to the fact that even if at the insertion station a test strip is placed onto the first transport section slightly obliquely, there is no danger of the strip contacting another test strip in the first transport section because there is only one test strip present in the first transport section at a time. During transfer of the test strip from the first to the second transport section a test strip inserted obliquely will be automatically aligned in a direction transverse to the transport direction. The way this is achieved is described below with reference to FIG. 3.

Figure 3:
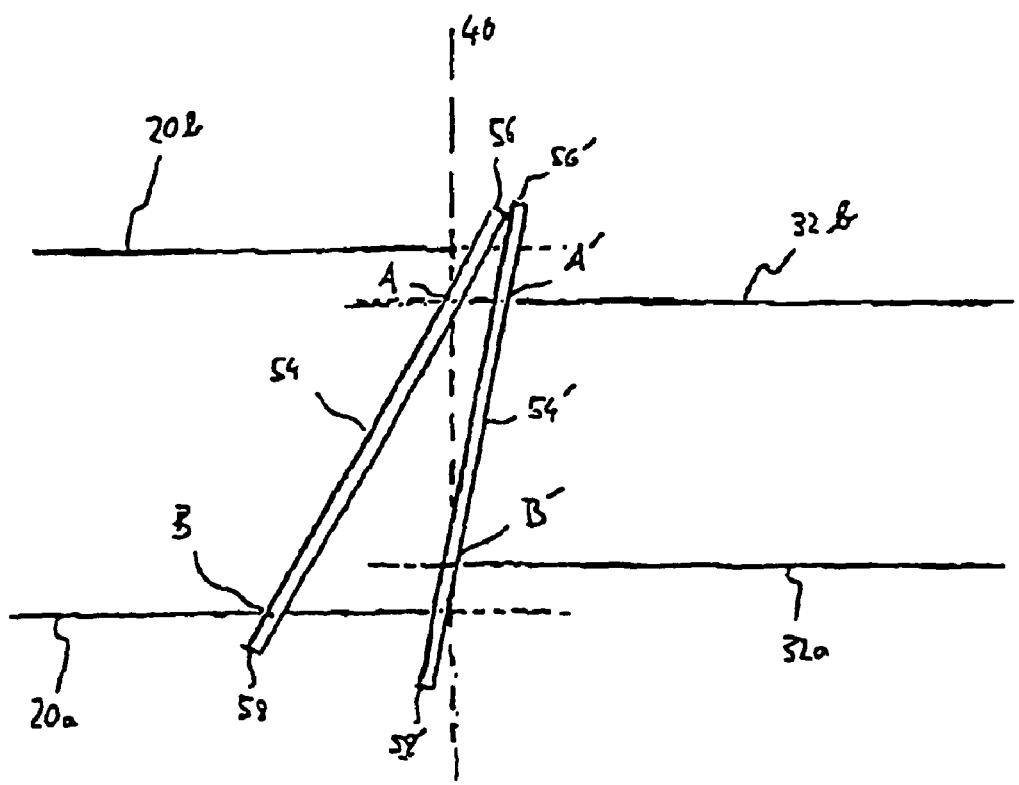
FIG. 3 is a plan view of the belts of the first and second transport sections and a test strip during alignment in the connecting region.

FIG. 3 is a plan view of the belts 20a, 20b of the first transport section and the belts 32a and 32b of the second transport section. The belt 34 has been omitted in this view because it runs deeper than the other belts in the connecting region, i.e. in the region of the apex line 40 of the second drum 24, and does not participate in test strip transfer. In FIG. 3, the belts 20a, 20b lie on the left side of the apex line 40 in the drawing plane and bend into the paper plane on the right side of the apex line 40, i.e. they extend below the drawing line in that region; the respective belt portion is indicated by the dashed lines. In FIG. 3 the belts 32a, 32b of the second transport section extend on the right side of the apex line 40 in the drawing plane and on the left side thereof below the drawing plane.

FIG. 3 shows a test strip 54 which was put onto the first transport section obliquely and which is moved to the connecting region at the first transport speed. The obliquity of the test strip 54 is exaggerated as an illustration. The first end 56 of the test strip is ahead of the second end 58 as seen in transport direction and is transferred at the contact point A onto the belt 32b of the second transport section, whereas the second end still rests on the belt 20a of the first transport section with contact point B. Now, the first end 56 of the test strip moves at the lower second transport speed, whereas the second end moves at the higher first transport speed, whereby the delay of the second end with respect to the first one is partly made up, i.e. the test strip is rotated toward a transverse position. The rotation lasts until the second end of the test strip, too, has been transferred onto the second transport section. The test strip at this later point of time is also shown in FIG. 3 and designated by 54'. The distances A, A' as measured between the contact points of the test strip ends in transport direction are to the distances B, B' as measured between the contact points of the test strip ends in transport direction approximately as the second transport speed is to the first transport speed. This shows that automatic alignment of the test strip in the connecting region is more effective the greater the difference between the two transport speeds is.

As mentioned above, the obliquity of the test strip 54 in FIG. 3 is largely exaggerated. In reality, the slit 16 already provides for relative precise alignment. In the connecting region, an almost perfect perpendicular alignment with respect to the transport direction is achieved.

Alignment of the test strip in the connecting region works particularly well when the belts 32a, 32b extend axially between the belts 20a, 20b, as shown in FIG. 3. If the belts 32a, 32b were outside the belt pair 20a, 20b, the first end 56 of the test strip would rest on both the belts 20b and 32b for a short time during transfer, and the rotation would thus start later and be less complete.

In the illustrated embodiment of the test strip analysis apparatus according to the invention the test strip is stopped and measured as it lies on the belts 32a, 32b and 34. For this purpose, the stop element 50 is moved into its blocking position wherein the pins 52 of the stop element 50 project into the conveying surface of the second transport section shortly before the test strip to be measured reaches the measuring position. The test strip 52 is caught at the pins 52 in its measuring position. In case the test strip has been turned in the second transport section, for example due to vibrations, it can then align transversely with respect to the transport section while resting at the pins 52. The test strip (designated by 44 in FIG. 2) is held by the stop element 50 for the duration of the measurement. Afterwards, the stop element 50 is moved into its release position wherein the pins 52 in FIG. 2 are raised and the test strip 44 is released.

In the illustrated embodiment the test strip analysis apparatus comprises a printer 60 (c.f. FIGS. 1 and 2) and a display panel 62 integrated in the housing 14 (c.f. FIG. 1). Thus, the result of the test strip analysis can immediately be read and recorded. The analysis apparatus shown further has means for connecting a bar-code reader and a keyboard that can be used for inputting, for example, patient related data required for recording the analysis results. The analysis apparatus has a recess at its lower side for accommodating a keyboard.

What is claimed is:

1. A test strip analysis apparatus for analyzing elongated test strips, with at least one test field, for detecting substances therein, whereupon the reflectivity or transmissivity of the at least one test field changes during a specific reaction period based on a concentration level of a substance to be detected, said apparatus comprising:
   a housing that defines an insertion station for receiving a test strip to be analyzed;
   an optical measuring unit for measuring the test strip;
   a transport device for transporting the test strip from the insertion station to the optical measuring unit within a desired reaction period for the test strip, wherein the transport device comprises first and second transport sections interconnected through a connecting region and driven independently of one another, such that the first transport section is configured to solely transport the test strip at a higher first transport speed from the insertion station to the connecting region, and the second transport section is configured to solely transport the test strip at a slower second transport speed from the connecting region to the optical measuring unit; and
   a sensor for detecting a test strip at the insertion station.

2. A test strip analysis apparatus according to claim 1, wherein the first and second transport sections have at least two continuous belts each, forming a conveying surface for a test strip placed across the belts, the conveying surfaces of the first and second transport sections being arranged at least approximately in the same plane and adjoining one another in the connecting region.

3. A test strip analysis apparatus according to claim 1, wherein the insertion station is defined by a slit formed in the housing through which a wetted test strip can be placed onto the conveying surface of the first transport section.

4. A test strip analysis apparatus according to claim 1, further comprising an indicator for indicating whether a test strip is present in the first transport section.

5. A test strip analysis apparatus according to claim 1, further comprising a printer.

6. A test strip analysis apparatus according to claim 1, further comprising a display panel.

7. A test strip analysis apparatus according to claim 1, further comprising means for inputting data associated with said test strip into a computer-accessible memory.

8. A test strip analysis apparatus according to claim 7, wherein said means for inputting is a keyboard and said housing further comprises a recess for accommodating said keyboard.

9. A test strip analysis apparatus for analyzing elongated test strips, with at least one test field, for detecting substances therein, whereupon the reflectivity or transmissivity of the at least one test field changes during a specific reaction period based on a concentration level of a substance to be detected, said apparatus comprising:
    a housing that defines an insertion station for receiving a test strip to be analyzed;
    an optical measuring unit for measuring the test strip;
    a transport device for transporting the test strip from the insertion station to the optical measuring unit within a desired reaction period for the test strip, wherein the transport device comprises first and second transport sections interconnected through a connecting region and driven independently of one another, such that the first transport section is configured to solely transport the test strip at a higher first transport speed from the insertion station to the connecting region, and the second transport section is configured to solely transport the test strip at a slower second transport speed from the connecting region to the optical measuring unit;
    wherein the first and second transport sections have at least two continuous belts each, forming a conveying surface for a test strip placed across the belts, the conveying surfaces of the first and second transport sections being arranged at least approximately in the same plane and adjoining one another in the connecting region;
    wherein the transport device comprises first, second and third drums arranged parallel to one another in one plane, the belts of the first transport section being stretched between the first drum and freely rotating rollers integrated in the second drum and being driven by the first drum at the first transport speed, and the belts of the second transport section being stretched between the second and third drums and being driven by the second drum or by the third drum at the second transport speed.

10. A test strip analysis apparatus according to claim 9, wherein the belts of the second transport section lie axially between the belts of the first transport section on the second drum.

11. A test strip analysis apparatus according to claim 9, wherein the second transport section comprises a third belt that is stretched between the second and third drums, and arranged axially between the first two belts, but runs in an annular groove provided in the second drum that has a depth such that the belt does not contact a test strip located in the connecting region.

12. A test strip analysis apparatus for analyzing elongated test strips, with at least one test field, for detecting substances therein, whereupon the reflectivity or transmissivity of the at least one test field changes during a specific reaction period based on a concentration level of a substance to be detected, said apparatus comprising:
    a housing that defines an insertion station for receiving a test strip to be analyzed;
    an optical measuring unit for measuring the test strip;
    a transport device for transporting the test strip from the insertion station to the optical measuring unit within a desired reaction period for the test strip, wherein the transport device comprises first and second transport sections interconnected through a connecting region and driven independently of one another, such that the first transport section is configured to solely transport the test strip at a higher first transport speed from the insertion station to the connecting region, and the second transport section is configured to solely transport the test strip at a slower second transport speed from the connecting region to the optical measuring unit;
    wherein the first and second transport sections have at least two continuous belts each, forming a conveying surface for a test strip placed across the belts, the conveying surfaces of the first and second transport sections being arranged at least approximately in the same plane and adjoining one another in the connecting region; and
    a stop element provided in a region of the measuring unit, said stop element being movable between a blocking position wherein a test strip located on the conveying surface of the second transport section aligns with a measuring position when stopped by the stop element and a release position when the test strip is released by the stop element.

13. A test strip analysis apparatus according to claim 12, wherein the stop element comprises two parallel pins which are mounted in spaced relation to one another on a holding device arranged transverse to a transport direction of the second transport section, wherein the two parallel pins project into a surface plane of the second transport section when the stop element is in its blocking position.

14. A test strip analysis apparatus according to claim 13, wherein the stop element has further blocking positions wherein the parallel pins project into the plane of the conveying surface of the second transport section in various locations.

* * * * *